United States Patent [19]

Higashimura et al.

[11] Patent Number: 5,605,876
[45] Date of Patent: Feb. 25, 1997

[54] HERBICIDAL COMPOSITION HAVING A REDUCED PHYTOTOXICITY

[75] Inventors: Minoru Higashimura, Ibaraki; Atsuhiko Yuda, Kawachinagano; Masakazu Shibayama, Takatsuki, all of Japan

[73] Assignee: Nihon Nohyaku Co. Ltd., Tokyo, Japan

[21] Appl. No.: 524,098

[22] Filed: Aug. 18, 1995

Related U.S. Application Data

[63] Continuation of Ser. No. 191,540, Feb. 4, 1994, abandoned.

[30] Foreign Application Priority Data

Feb. 6, 1993 [JP] Japan .................. 5-042065

[51] Int. Cl.⁶ .................. A01N 25/30; A01N 25/32; A01N 43/56
[52] U.S. Cl. .................. 504/103; 504/112; 504/282; 71/DIG. 1
[58] Field of Search ................. 504/282, 103, 504/112; 71/DIG. 1

[56] References Cited

U.S. PATENT DOCUMENTS

| | | | |
|---|---|---|---|
| 4,789,396 | 12/1988 | Arai et al. | 71/94 |
| 5,032,165 | 7/1991 | Miura et al. | 71/92 |
| 5,073,189 | 12/1991 | Bell | 71/92 |
| 5,112,384 | 5/1992 | Miura et al. | 71/92 |

FOREIGN PATENT DOCUMENTS

| | | |
|---|---|---|
| 0273799A | 7/1988 | European Pat. Off. . |
| 3163063 | 7/1991 | Japan . |
| 3-246204A | 11/1991 | Japan . |
| 4-59706A | 2/1992 | Japan . |
| 4-211065 | 8/1992 | Japan . |
| 2031605T | 4/1989 | Spain . |
| 1488285 | 10/1977 | United Kingdom . |
| 9202509 | 8/1991 | WIPO . |

*Primary Examiner*—S. Mark Clardy
*Attorney, Agent, or Firm*—Cushman Darby & Cushman IP Group of Pillsbury Madison & Sutro LLP

[57] ABSTRACT

A herbicidal composition having a reduced phytotoxicity which comprises at least one compound selected from 3-substituted phenylpyrazole derivatives such as ET-751 represented by the general formula (I):

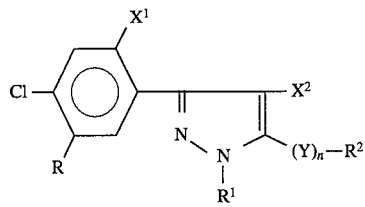

(wherein R is a substituent such as an alkoxy group, each of $R^1$ and $R^2$ is a substituent such as a lower alkyl group, Y is an oxygen atom or the like, and each of $X^1$ and $X^2$ is a halogen atom) and at least one specific anionic surfactant.

5 Claims, No Drawings

HERBICIDAL COMPOSITION HAVING A REDUCED PHYTOTOXICITY

This is a continuation of application Ser. No. 08/191,540, filed on Feb. 4, 1994, which was abandoned upon the filing hereof.

BACKGROUND OF THE INVENTION

This invention relates to a herbicidal composition containing as an active ingredient(s) at least one compound selected from 3-substituted phenylpyrazole derivatives represented by the general formula (I):

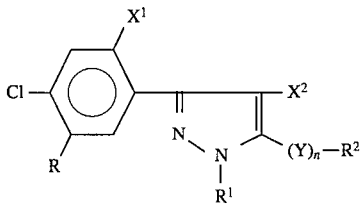

[wherein R is

(wherein $R^3$ is a $C_1$–$C_6$ alkyl group, a $C_1$–$C_6$ haloalkyl group, a $C_2$–$C_6$ alkenyl group or a $C_2$–$C_6$ alkynyl group, and $Y^1$ is —O— or —S—),

—$Y^2CH(R^4)CO$—$OR^5$ (wherein $R^4$ is a hydrogen atom or a $C_1$–$C_6$ alkyl group, $R^5$ is a hydrogen atom, a $C_1$–$C_6$ alkyl group, a $C_1$–$C_6$ lower haloalkyl group, a $C_2$–$C_6$ alkenyl group or a $C_2$–$C_6$ alkynyl group, and $Y^2$ is —O—, —S— or —NH—),

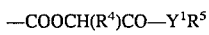

(wherein $R^4$, $R^5$ and $Y^1$ are as defined above), or

(wherein $R^6$ is a $C_1$–$C_6$ alkyl group, a $C_2$–$C_6$ alkenyl group or a $C_2$–$C_6$ alkynyl group), $R^1$ is a $C_1$–$C_6$ alkyl group, $R^2$ is a hydrogen atom, a $C_1$–$C_6$ alkyl group or a $C_1$–$C_6$ haloalkyl group, $X^1$ and $X^2$, which may be the same or different, are halogen atoms, Y is —O—, —S—, —SO— or —$SO_2$—, and n is zero or 1], said herbicidal composition further containing as an additive(s) at least one anionic surfactant selected from the following;

polyoxyethylene styryl phenyl ether sulfates, polyoxyethylene styryl phenyl ether phosphates, polyoxyethylene styryl phenyl ether sulfonates, polyoxyethylene styryl phenyl ether carbonates, $C_8$–$C_{18}$ alkyl sulfates, ligninsulfonates, condensation products of naphthalenesulfonate and formaldehyde, phenylsulfonates, polycarbonates, condensation products of cresol and formaldehyde, and fatty acid alkyltaurines.

Of the substituents of the 3-substituted phenylpyrazole derivative of the general formula (I) used in the present invention, each alkyl group is a linear or branched alkyl group having 1 to 6 carbon atoms, each haloalkyl group is a substituted alkyl group having as the substituent(s) one or more halogen atoms which may be the same or different and are selected from the group consisting of chlorine, fluorine, iodine and bromine atoms, each lower alkenyl group is a linear or branched alkenyl group having 2 to 6 carbon atoms, and each alkynyl group is a linear or branched alkynyl group having 2 to 6 carbon atoms.

RELATED ART

The 3-substituted phenylpyrazole derivative of the general formula (I) is a compound described in Japanese Patent Unexamined Publication Nos. 3-163063 and 4-211065. As a herbicide, said derivative has an excellent herbicidal activity against all of herbaceous weeds which are harmful to upland farming. Particularly when applied for wheat (barley, oats or rye) cropping, said derivative exhibits a marked herbicidal effect on typical weeds such as cleavers (*Galium aparine*), chickweed (*Stellaria media*), birdseye speedwell (*Veronica persica*), sentless chamomile (*Matricaria inodora*), purple deadnettle (*Lamium purpureum*), henbit (*Lamium amplexicaule*), shepherd's purse (*Capsella bursapostoris*), marsh yellowcress (*Rorippa islandica*), sticky chichweed (*Cerastium viscosum*), common lambsquarters (*Chenopodium album*), tufted knotweed (*Polygomum longisetum*), prostrate knotweed (*Polygonum aviculare*), etc.

However, the following was found. When the 3-substituted phenylpyrazole derivative of the general formula (I) is applied after being prepared into a herbicide containing said derivative as an active ingredient, for example, a suspension concentrate, emulsifiable concentrate, wettable powder, or water dispersible granules, said derivative exhibits an excellent herbicidal effect on the above-exemplified various herbaceous weeds. But, it tends to promote phytotoxicity such as growth inhibition or leaf burn in wheat, barley, oats, rye, etc., depending on the kind of a surfactant used in the herbicide.

SUMMARY OF THE INVENTION

The present inventors earnestly investigated for solving such problems and consequently found that the incorporation of at least one specific anionic surfactant into a herbicide containing at least one compound selected from 3-substituted phenylpyrazole derivatives of the general formula (I) as an active ingredient(s), maintains the inherent herbicidal effect on herbaceous weeds and reduces the phytotoxicity to wheat, barley, oats and rye, whereby the present invention has been accomplished.

DETAILED DESCRIPTION OF PREFERRED EMBODIMENTS

Of the substituents in the present 3-substituted phenylpyrazol derivatives of the general formula (I), preferable as R are alkoxycarbonylalkyloxy groups, such as methoxycarbonylmethyloxy, ethoxycarbonylmethyloxy, n-propoxycarbonylmethyloxy, i-propoxycarbonylmethyloxy and alkylthiocarbonylalkyloxycarbonyl groups, such as methylthiocarbonylmethyloxycarbonyl, ethylthiocarbonylmethyloxycarbonyl and the like.

Preferable as $R^1$ are alkyl groups such as methyl, ethyl, n-propyl, i-propyl and the like. Particularly preferable as $R^1$ is methyl groups.

Preferable as $R^2$ are alkyl groups such as methyl, ethyl, n-propyl, i-propyl and haloalkyl groups such as fluoromethyl, difluoromethyl, trifluoromethyl and the like. Particularly preferable as $R^2$ is difluoromethyl group.

Preferable as $X^1$ are halogen atoms such as chlorine atom, fluorine atom, bromine atom, iodine atom, and the like. Particularly preferable as $X^1$ is fluorine atom.

Preferable as $X^2$ are halogen atoms such as chlorine atom, fluorine atom, bromine atom, iodine atom and the like. Particularly preferable as $X^2$ is fluorine atom or bromine atom.

Preferable as Y is oxygen or sulfur atom and the like. Particularly preferable as Y is oxygen atom.

As typical examples of the compound(s) selected from 3-substituted phenylpyrazole derivatives of the general formula (I), i.e., the active ingredient(s) used in the present invention, compounds of the general formula (1) in which $R^1$ is $CH_3$ are listed in Table 1, but they are not intended in any way to limit the scope of the present invention.

General formula (I):

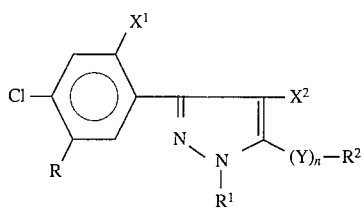

TABLE 1

| No. | R | $R^2$ | $X^1$ | $X^2$ | (Y) n | Physical properties |
|---|---|---|---|---|---|---|
| 1 | $OCH_2CH=CH_2$ | $CH_3$ | Cl | Cl | S | nD 1.6131 (25.3° C.) |
| 2 | $OCH_2CH=CH_2$ | $CHF_2$ | Cl | Cl | O | nD 1.5536 (28.4° C.) |
| 3 | $OCH_2CH=CH_2$ | $CHF_2$ | F | Cl | O | m.p. 63.7–64.1° C. |
| 4 | $SCH_2CH=CH_2$ | $CH_3$ | Cl | Cl | S | paste |
| 5 | $SCH_2CH=CH_2$ | $CHF_2$ | Cl | Cl | O | m.p. 52.0–55.0° C. |
| 6 | $SCH_2CH=CH_2$ | $CHF_2$ | F | Cl | O | nD 1.5670 (17.9° C.) |
| 7 | $OCH_2C\equiv CH$ | $CH_3$ | Cl | Cl | S | m.p. 71.5° C. |
| 8 | $OCH_2C\equiv CH$ | $CHF_2$ | Cl | Cl | O | m.p. 84.0° C. |
| 9 | $OCH_2C\equiv CH$ | $CHF_2$ | F | Cl | O | m.p. 98.0–98.1° C. |
| 10 | $SCH_2C\equiv CH$ | $CH_3$ | Cl | Cl | S | m.p. 94.5° C. |
| 11 | $SCH_2C\equiv CH$ | $CHF_2$ | Cl | Cl | O | m.p. 127–129° C. |
| 12 | $SCH_2C\equiv CH$ | $CHF_2$ | F | Cl | O | m.p. 82.8° C. |
| 13 | $OCH_2COOCH_3$ | $CH_3$ | Cl | Cl | S | m.p. 126.2° C. |
| 14 | $OCH_2COOCH_3$ | $CHF_2$ | Cl | Cl | O | m.p. 119.8° C. |
| 15 | $OCH_2COOCH_3$ | $CHF_2$ | Cl | Br | O | m.p. 133.8° C. |
| 16 | $OCH_2COOCH_3$ | $CHF_2$ | F | Cl | O | m.p. 122.8–123.1° C. |
| 17 | $OCH_2COOC_2H_5$ | $CH_3$ | Cl | Cl | S | m.p. 106.5° C. |
| 18 | $OCH_2COOC_2H_5$ | $CHF_2$ | Cl | Cl | O | m.p. 102.3° C. |
| 19 | $OCH_2COOC_2H_5$ | $CHF_2$ | F | Cl | O | m.p. 126.7° C. |
| 20 | $OCH_2COOC_3H_7$-n | $CHF_2$ | Cl | Cl | O | m.p. 89.7° C. |
| 21 | $OCH_2COOC_3H_7$-n | $CHF_2$ | F | Cl | O | m.p. 97.6–97.8° C. |
| 22 | $OCH_2COOC_3H_7$-i | $CHF_2$ | Cl | Cl | O | m.p. 106.0° C. |
| 23 | $OCH_2COOC_3H_7$-i | $CHF_2$ | F | Cl | O | m.p. 120.3–120.5° C. |
| 24 | $OCH_2COOCH_2CH=CH_2$ | $CHF_2$ | Cl | Cl | O | m.p. 84.7° C. |
| 25 | $OCH_2COOCH_2CH=CH_2$ | $CHF_2$ | F | Cl | O | m.p. 89.2–89.4° C. |
| 26 | $OCH_2COOCH_2C\equiv CH$ | $CHF_2$ | Cl | Cl | O | m.p. 119.6° C. |
| 27 | $OCH_2COOCH_2C\equiv CH$ | $CHF_2$ | F | Cl | O | m.p. 99.0° C. |
| 28 | $OCH(CH_3)COOH$ | $CH_3$ | Cl | Cl | S | m.p. 191–194° C. |
| 29 | $OCH(CH_3)COOCH_3$ | $CH_3$ | Cl | Cl | S | m.p. 90–93° C. |
| 30 | $OCH(CH_3)COOCH_3$ | $CHF_2$ | F | Cl | O | m.p. 95.6° C. |
| 31 | $OCH(CH_3)COOC_2H_5$ | $CH_3$ | Cl | Cl | S | nD 1.5763 (28.8° C.) |
| 32 | $OCH(CH_3)COOC_2H_5$ | $CHF_2$ | Cl | Cl | O | nD 1.5238° C. (25.7° C.) |
| 33 | $OCH(CH_3)COOC_2H_5$ | $CHF_2$ | Cl | Br | O | nD 1.5396 (20.8° C.) |
| 34 | $OCH(CH_3)COOC_2H_5$ | $CHF_2$ | F | Cl | O | m.p. 67.0–67.2° C. |
| 35 | $OCH(CH_3)COOC_3H_7$-i | $CH_3$ | Cl | Cl | S | m.p. 87–90° C. |
| 36 | $SCH(CH_3)COOCH_3$ | $CHF_2$ | Cl | Cl | O | nD 1.5654 (19.8° C.) |
| 37 | $SCH(CH_3)COOCH_3$ | $CHF_2$ | F | Cl | O | nD 1.5494 (25.0° C.) |
| 38 | $SCH(CH_3)COOC_2H_5$ | $CHF_2$ | Cl | Cl | O | nD 1.5565 (28.0° C.) |
| 39 | $SCH(CH_3)COOC_2H_5$ | $CHF_2$ | F | Cl | O | nD 1.5328 (18.0° C.) |
| 40 | $NHCH(CH_3)COOCH_3$ | $CH_3$ | Cl | Cl | S | m.p. 144.2° C. |
| 41 | $NHCH(CH_3)COOC_2H_5$ | $CH_3$ | Cl | Cl | S | paste |
| 42 | $NHCH(CH_3)COOC_2H_5$ | $CHF_2$ | Cl | Cl | O | nD 1.5371 |

TABLE 1-continued

| No. | R | $R^2$ | $X^1$ | $X^2$ | (Y)n | Physical properties |
|---|---|---|---|---|---|---|
| 43 | $NHCH(CH_3)COOC_2H_5$ | $CHF_2$ | F | Cl | O | nD 1.5264 (23.4° C.) |
| 44 | $COOCH_2COOCH_3$ | $CHF_2$ | Cl | Cl | O | m.p. 74.4° C. |
| 45 | $COOCH_2COOCH_3$ | $CHF_2$ | F | Cl | O | nD 1.5350 (26.6° C.) |
| 46 | $COOCH_2COSCH_3$ | $CHF_2$ | Cl | Cl | O | |
| 47 | $COOCH_2COSCH_3$ | $CHF_2$ | F | Cl | O | |
| 48 | $COOCH_2COOC_2H_5$ | $CHF_2$ | Cl | Cl | O | m.p. 57.2° C. |
| 49 | $COOCH_2COOC_2H_5$ | $CHF_2$ | F | Cl | O | nD 1.5362 (27.3° C.) |
| 50 | $COOCH_2COSC_2H_5$ | $CHF_2$ | Cl | Cl | O | nD 1.5763 (23.4° C.) |
| 51 | $COOCH_2COSC_2H_5$ | $CHF_2$ | F | Cl | O | nD 1.5536 (20.7° C.) |
| 52 | $COOCH_2COOC_3H_7$-i | $CHF_2$ | Cl | Cl | O | nD 1.5289 (27.3° C.) |
| 53 | $COOCH_2COOC_3H_7$-i | $CHF_2$ | F | Cl | O | |
| 54 | $COOCH_2COSC_3H_7$-i | $CHF_2$ | Cl | Cl | O | nD 1.5684 (24.0° C.) |
| 55 | $COOCH_2COSC_3H_7$-i | $CHF_2$ | F | Cl | O | |
| 56 | $COOCH_2COOCH_2CH=CH_2$ | $CHF_2$ | Cl | Cl | O | m.p. 45.4° C. |
| 57 | $COOCH_2COOCH_2CH=CH_2$ | $CHF_2$ | F | Cl | O | (20.2° C.) |
| 58 | $COOCH_2COOCH_2C\equiv CH$ | $CHF_2$ | Cl | Cl | O | m.p. 79.3° C. |
| 59 | $COOCH_2COOCH_2C\equiv CH$ | $CHF_2$ | F | Cl | O | |
| 60 | $COOCH(CH_3)COOCH_3$ | $CHF_2$ | Cl | Cl | O | nD 1.5370 (25.7° C.) |
| 61 | $COOCH(CH_3)COOCH_3$ | $CHF_2$ | F | Cl | O | nD 1.5314 (23.0° C.) |
| 62 | $COOCH(CH_3)COOC_2H_5$ | $CHF_2$ | Cl | Cl | O | nD 1.5672 (26.0° C.) |
| 63 | $COOCH(CH_3)COOC_2H_5$ | $CHF_2$ | F | Cl | O | nD 1.5212 (14.1° C.) |
| 64 | $COOCH_2C\equiv CH$ | $CHF_2$ | Cl | Cl | O | m.p. 78.5° C. |
| 65 | $COOCH_3$ | $CHF_2$ | Cl | Cl | O | m.p. 63.9° C. |
| 66 | $COOCH_3$ | $CHF_2$ | F | Cl | O | nD 1.5430 (17.0° C.) |
| 67 | $COOC_2H_5$ | $CH_3$ | Cl | Cl | S | nD 1.6029 (20.1° C.) |
| 68 | $COOC_2H_5$ | $CHF_2$ | Cl | Cl | O | nD 1.5446 (26.8° C.) |
| 69 | $COOC_2H_5$ | $CHF_2$ | F | Cl | O | nD 1.5320 (21.0° C.) |
| 70 | $OCH_2CH=CH_2$ | $CHF_2$ | Cl | Cl | NH | m.p. 80.6° C. |
| 71 | $OCH_2C\equiv CH$ | $CHF_2$ | Cl | Cl | NH | m.p. 118.9° C. |
| 72 | $OCH_2COOCH_3$ | i-$C_3H_7$ | Cl | Cl | — | paste |
| 73 | $OCH_2CH=CH_2$ | i-$C_3H_7$ | Cl | Cl | — | paste |
| 74 | $OCH_2C\equiv CH$ | i-$C_3H_7$ | Cl | Cl | — | paste |
| 75 | $SCH_2COOCH_3$ | t-$C_4H_9$ | Cl | Cl | — | paste |
| 76 | $OCH_2CH=CH_2$ | $CH_2Br$ | Cl | Cl | — | paste |

As the specific anionic surfactant(s) used in the present invention, one or more anionic surfactants can be selected from the group consisting of, for example, sodium, potassium, calcium, ammonium, alkylamine or alkanolamine salts of polyoxyethylene styryl phenyl ether sulfates, polyoxyethylene styryl phenyl ether phosphates, polyoxyethylene styryl phenyl ether sulfonates or polyoxyethylene styryl phenyl ether carbonates; sodium, potassium, calcium or ammonium salts of $C_8$–$C_{18}$ alkyl sulfates, ligninsulfonates, condensation products of naphthalenesulfonate and formaldehyde, phenylsulfonates, polycarbonates, and condensation products of cresol and formaldehyde; and fatty acid alkyltaurines. Of these, there are preferably used sodium, potassium, calcium, ammonium, alkylamine or alkanolamine salts of polyoxyethylene styryl phenyl ether sulfates, polyoxyethylene styryl phenyl ether phosphates, polyoxyethylene styryl phenyl ether sulfonates, polyoxyethylene styryl phenyl ether carbonates. Of these, particularly there are preferably used sodium, potassium, calcium, ammonium of polyoxyethylene styryl phenyl ether sulfates or polyoxyethylene styryl phenyl ether phosphates. The above polyoxyethylene type anionic surfactants have mono or poly styryl groups and either of these forms can be used.

As to the proportion of the anionic surfactant(s) used in the present invention, it is sufficient that the anionic surfactant(s) is present in the herbicidal composition in a proportion of 0.1 to 80 parts by weight, preferably 0.5 to 60 parts by weight, per 100 parts by weight of the herbicidal composition.

The herbicidal composition of the present invention may contain a nonionic surfactant. In this case, the anionic surfactant(s) should be used in an amount sufficient to prevent the phytotoxicity of the nonionic surfactant.

For applying the herbicidal composition of the present invention, it may be prepared into suitable forms according to an ordinary manner for preparation of agrochemicals, depending on purposes. For example, said composition is blended with one or more materials selected from the group consisting of solid carriers and liquid carriers, and optionally adjuvants, etc. and prepared into a preparation form such as a suspension concentrate, emulsifiable concentrate, wettable powder, water dispersible glanules, emulsion concentrate, or the like.

The herbicidal composition of the present invention is useful for upland farming particularly as a selective herbicidal composition for wheat, barley, oats and rye. Furthermore, said composition can be used in admixture with other pesticidally active ingredients for the purpose of, for example, reducing the dosage or expanding the spectrum of controllable weeds. As the other pesticidally active ingredients used for such a purpose, there can be exemplified, 3-p-cumenyl-1,1-dimethylurea (Common name: Isoproturon), ethyl (±)-2-[4-(6-chloro-1,3-benzoxazol-2-yloxy)phenoxy]propionate (Common name: Fenoxaprop-ethyl), methyl (RS)-2-[4-(2,4-dichlorophenoxy)phenoxy]propionate (Common name: Diclofop-methyl), (RS)-2-[2-[4-(3,5-dichloro-2-pyridyloxy)phenoxy]propionyl]-1,2-oxazolidine (Common name: Isoxapyrifop), 2-[1-(ethoxyimino)propyl]-3-hydroxy-5-mesitylcyclohex-2-enone (Common name: Tralkoxydim), methyl 2-(4-methoxy-6-methyl-1,3,5-triazin-2-ylcarbamoylsulfamoyl)benzoate (Common name: Metsulfuron-methyl), 2',4'-difluoro-2-α,α,α-trifluoro-m-tolyloxy)nicotinanilide (Common name: Diflufenican), N-(1-ethylpropyl)-2,6-dinitro-3,4-xylidine (Common name: Pendimethalin), 0-[5-(2-chloro-α,α,α-trifluoro-p-tolyloxy)-2-nitrobenzoyl]glycolate (Common name: Fluoroglycofen-ethyl), methyl 5-(2,4-dichlorophenoxy)-2-nitrobenzoate (Common name: Bifenox), 3,5-dibromo-4-hydroxybenzonitrile (Common name: Bromoxynil), 3-(3-chloro-p-tolyl)-1,1-dimethylurea (Common name: Chlorotoluron), 2-(4-chloro-6-ethylamino-1,3,5-triazin-2-ylamino)-2-methylpropionitril (Common name: Cyanazine), methyl (±)-6-(4-isopropyl-4-methyl-5-oxo-2-imidazolin-2-yl)-m-toluate and methyl (±)-2-(4-isopropyl-4-methyl-5-oxo-2-imidazolin-2-yl)-p-toluate (Common name: Imazamethabenz-methyl), 4-hydroxy-3,5-diiodobenzonitrile (Common name: Ioxynil), N-[3-(1-ethyl-1-methylpropyl)-1,2-oxazol-5-yl]-2,6-dimethoxybenzamide (Common name: Isoxaben), 1-(1,3-benzothiazol-2-yl)-1,3-dimethylurea (Common name: Methabenzthiazuron), 3-(3-chloro-4-methoxyphenyl)-1,1-dimethylurea (Common name: Metoxuron), S-2,3,3-trichloroallyl di-isopropyl(thiocarbamate) (Common name: Tri-allate), methyl 2-[4-methoxy-6-methyl-1,3,5-triazin-2-yl(methyl)carbamoylsulfamoyl]benzoate (Common name: Tribenuron-methyl), 1-(2-chlorophenylsulfonyl)-3-(4-methoxy-6-methyl-6-methyl-1,3,5-triazin-2-yl)urea (Common name: Chlorsulfuron), methyl 3-(4-methoxy-6-methyl-1,3,5-triazin-2-ylcarbamoylsulfamoyl)thiophen-2-carboxylate (Common name: Thifensulfuron-methyl), 1-[2-(2chloroethoxy)phenylsulfonyl]-3-(4-methoxy-6-methyl-1,3,5-triazin-2-yl)urea (Common name: Thiasulfuron), 1-[(N-methylsulfonyl-N-methylamino)sulfonyl]-3-(4,6-dimethoxypyrimidin-2-yl)urea (Common name: Amidosulfuron), 4-amino-3,5-dichloro-6-fluoro-2-pyridyloxyacetic acid (Common name: Fluoroxypyl), 3,6-dichloropyridine-2-carboxylic acid (Common name: Clopyralid), 7-chloro-3-methylquinoline-8-carboxylic acid (Common name: Quinmerac), 6-chloro-3-phenylpyridazin-4-yl S-octyl thiocarbonate (Common name: Pyridate), 4-chloro-o-tolyloxyacetic acid (Common name: MCPA), 2,4-dichlorophenoxyacetic acid (Common name: 2,4-D), (RS)-2-(4-chloro-o-tolyloxy)propionic acid (Common name: Mecoprop), salts thereof and esters thereof.

These herbicidal compounds may be used in the form of any of various preparations obtained by mixing with the composition of the present invention, or in the form of a mixture prepared just before application by mixing herbicidal compositions prepared from the herbicidal compound and the composition of the present invention, respectively.

Typical examples, comparative examples and test examples of the present invention are described below but they should not be construed as limiting the scope of the invention.

EXAMPLE 1

To 81.3 parts of water were added 10.0 parts of propylene glycol, 0.2 part of dioctyl sulfosuccinate sodium salt (NEOCOL YSK, Dai-ichi Kogyo Seiyaku Co., Ltd.), 5.0 parts of a polyoxyethylene styryl phenyl ether phosphate (Sorpol 7425, TOHO KAGAKU K.K.), 0.5 part of a defoaming agent (Silicone KM-73, Shin-Etsu Chemical Co., Ltd.) and 0.1 part of an antiseptic (Proxel GXL, ICI PLC), followed by dissolution and mixing by means of an agitator (HOMO MIXER, TOKUSHU KIKA IND. Co., Ltd.). Then, 2.5 parts of compound No. 19 was added and the resulting mixture was finely ground with a wet type grinder (DYNO-MILL Model KDL, Bachofen Co., Ltd.), after which 0.4 part of xanthan gum (RHODOPOL 23, Rhone Poulenc) was added, followed by uniform mixing. Thus, a suspension concentrate containing 2.5% of compound No. 19 was obtained.

EXAMPLE 2

To 81.3 parts of water were added 10.0 parts of propylene glycol, 0.2 part of dioctyl sulfosuccinate sodium salt (NEOCOL YSK), 5.0 parts of a polyoxyethylenestyryl phenyl ether sulfate (SP-7290P, TOHO KAGAKU K.K.), 0.5 part of a defoaming agent (Silicone KM-73) and 0.1 part of an antiseptic (Proxel GXL), followed by dissolution and mixing by means of an agitator (HOMO MIXER). Then, 2.5 parts of compound No. 19 was added and the resulting mixture was finely ground with a wet type grinder (DYNO-MILL Model KDL), after which 0.4 part of xanthan gum (RHODOPOL 23) was added, followed by uniform mixing. Thus, a suspension concentrate containing 2.5% of compound No. 19 was obtained.

EXAMPLE 3

To 81.3 parts of water were added 5.0 parts of ethylene glycol, 0.2 part of a polyoxyethylene nonyl phenyl ether (NPE-100, Asahi Denka Co., Ltd.), 10.0 parts of polyoxyethylene tristyrylphenol sulfate (SOPRPHOR FL, Rhone Poulenc), 0.5 part of a defoaming agent (Silicone KM-73) and 0.1 part of an antiseptic (Proxel GXL), followed by dissolution and mixing by means of an agitator (HOMO MIXER). Then, 2.5 parts of compound No. 19 was added and the resulting mixture was finely ground with a wet type grinder (DYNO-MILL Model KDL), after which 0.4 part of xanthan gum (RHODOPOL 23) was added, followed by uniform mixing. Thus, a suspension concentrate containing 2.5% of compound No. 19 was obtained.

EXAMPLE 4

To 84.3 parts of water were added 5.0 parts of ethylene glycol, 0.2 part of dioctyl sulfosuccinate sodium salt (NEOCOL YSK), 7.0 parts of calcium lignin-sulfonate (SAN-EKISU P-201, Sanyo-Kokusaku Pulp Co., Ltd.), 0.5 part of a defoaming agent (Silicone KM-73) and 0.1 part of an antiseptic (Proxel GXL), followed by dissolution and mixing by means of an agitator (HOMO MIXER). Then, 2.5 parts of compound No. 19 was added and the resulting mixture was finely ground with a wet type grinder (DYNO-MILL Model KDL), after which 0.4 part of xanthan gum (RHODOPOL 23) was added, followed by uniform mixing. Thus, a suspension concentrate containing 2.5% of compound No. 19 was obtained.

EXAMPLE 5

To 88.3 parts of water were added 5.0 parts of ethylene glycol, 0.2 part of a polyoxyethylene nonyl phenyl ether (NPE-100), 3.0 parts of a condensation product of naphthalenesulfonic acid and formaldehyde (Dispersogen A, Hoechst A.G.), 0.5 part of a defoaming agent (Silicone KM-73) and 0.1 part of an antiseptic (Proxel GXL), followed by dissolution and mixing by means of an agitator (HOMO MIXER). Then, 2.5 parts of compound No. 19 was added and the resulting mixture was finely ground with a wet type grinder (DYNO-MILL Model KDL), after which 0.4 part of xanthan gum (RHODOPOL 23) was added, followed by uniform mixing. Thus, a suspension concentrate containing 2.5% of compound No. 19 was obtained.

EXAMPLE 6

An emulsifiable concentrate containing 2.5% of compound No. 19 was obtained by mixing the following ingredients uniformly to effect dissolution: 78.5 parts of methylnaphthalene, 10.0 parts of N-methylpyrrolidone, 1.0 part of a polyoxyethylene nonyl phenyl ether (NPE-100), 8.0 parts of polyoxyethylene styryl phenyl ether sulfate (SP-7290P) and 2.5 parts of compound No. 19.

EXAMPLE 7

A wettable powder containing 2.5% of compound No. 19 was obtained by mixing and grinding 2.5 parts of compound No. 19, 1.0 part of a polyoxyethylene nonyl phenyl ether (NPE-100), 5.0 parts of a condensation product of naphthalenesulfonic acid and formaldehyde (New Kalgen 207, Takemoto Oil and Fat Co., Ltd.) and 91.5 parts of clay.

EXAMPLE 8

After uniform mixing of 2.5 parts of compound No. 19, 0.5 parts of a polyoxyethylene nonyl phenyl ether ammonium salt (Hitenol NO8, Dai-ichi Kogyo Seiyaku Co., Ltd.), 5.0 parts of calcium ligninsulfonate (SANEKISU P-201, Sanyo-Kokusaku Pulp Co., Ltd.), 25.0 parts of bentonite and 67.0 parts of clay, a proper amount of water was added. The resulting mixture was kneaded, extruded through 1.0 mm holes with a basket type granulator (Model RG-5, Kikusui Seisakusho LTD) and then dried by fluidized drying. Thus, a water disporsible granule containing 2.5% of compound No. 19 was obtained.

Comparative Example 1

A suspension concentrate containing 2.5% of compound No. 19 was obtained in the same manner as in Example 1, except that an alkyl phosphate ester salt (Electrostripper N, Kao Corp.) was used in place of the polyoxyethylene stryl phenyl ether phosphate (Sorpol 7425).

Comparative Example 2

A suspension concentrate containing 2.5% of compound No. 19 was obtained in the same manner as in Example 4, except that an α-olefinsulfonic acid (RIBORAN 440, Lion Co., Ltd.) was used in place of calcium ligninsulfonate (SAN-EKISU P-201).

Comparative Example 3

A wettable powder containing 2.5% of compound No. 19 was obtained in the same manner as in Example 7, except that a polyoxyethylene fatty amide ether sulfate (NISSAN-SAN-AMIDO, Nippon Oils and Fats Co., Ltd.) was used in place of the condensation product between naphthalenesulfonic acid and formaldehyde (New Kalgen 207).

Test Example 1

Herbicidal effect and phytotoxicity test

A plastic pot with a diameter of 12 cm and a height of 12 cm was filled with sifted upland soil and seeded with wheat (WE), cleavers (*Galium aparine*, GA) and birdseye speedwell (*Veronica persica*, BS) so as to adjust the depth of covering soil to 1 cm, and these plants were grown in a greenhouse.

When the wheat was grown to a leaf stage of 3 and the cleavers (GA) and birdseye speedwell (BS) were grown to a leaf stage of 1, a liquid chemical containing a predetermined concentration of each of the preparations exemplified in the examples and the comparative examples was sprayed uniformly on the stalk and leaves in a spray volume of 300 liters per hectare by the use of a napsack sprayer.

After being treated with the preparation, the plants were grown in the greenhouse for 14 days and the phytotoxicity to wheat and the herbicidal effect on the weeds were visually judged in the range of zero (no phytotoxicity or no herbicidal effect) to 100 (complete kill).

The results obtained are shown in Table 2.

TABLE 2

| Example No. | Dosage g/ha | Phytotoxicity Wheat | Herbicidal activity GA | BS |
|---|---|---|---|---|
| Example 1 | 5 | 0 | 100 | 100 |
|  | 10 | 2 | 100 | 100 |
| Example 2 | 5 | 0 | 100 | 100 |
|  | 10 | 3 | 100 | 100 |
| Example 3 | 5 | 0 | 100 | 100 |
|  | 10 | 2 | 100 | 100 |
| Example 4 | 5 | 0 | 100 | 100 |
|  | 10 | 1 | 100 | 100 |
| Example 5 | 5 | 0 | 100 | 100 |
|  | 10 | 2 | 100 | 100 |
| Example 6 | 5 | 2 | 100 | 100 |
|  | 10 | 7 | 100 | 100 |
| Example 7 | 5 | 0 | 100 | 100 |
|  | 10 | 2 | 100 | 100 |
| Example 8 | 5 | 0 | 100 | 100 |
|  | 10 | 3 | 100 | 100 |
| Comparative Example 1 | 5 | 25 | 100 | 100 |
|  | 10 | 40 | 100 | 100 |
| Comparative Example 2 | 5 | 25 | 100 | 100 |
|  | 10 | 40 | 100 | 100 |
| Comparative Example 3 | 5 | 20 | 100 | 100 |
|  | 10 | 30 | 100 | 100 |

As shown in Table 2, it is clear that the herbicidal compositions containing one or more specific anionic surfactants of the present invention have a marked herbicidal effect on weeds emerging during wheat cropping and a reduced phytotoxicity to wheat.

What is claimed is:

1. A method of reducing phytotoxicity to crops selected from the group consisting of wheat, barley, oats and rye, of herbicidal compositions comprising as an active ingredient at least one compound selected from 3-substituted phenylpyrazole derivatives represented by the general formula (I):

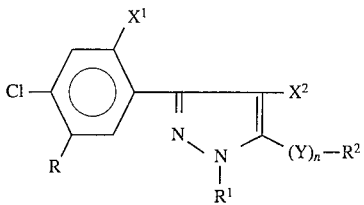

wherein R is

—Y$^1$R$^3$ (wherein R$^3$ is a C$_1$–C$_6$ alkyl group, a C$_1$–C$_6$ haloalkyl group, a C$_2$–C$_6$ alkenyl group or a C$_2$–C$_6$ alkynyl group, and Y$^1$ is —O— or —S—),

—Y$^2$CH(R$^4$)CO—OR$^5$ (wherein R$^4$ is a hydrogen atom or a C$_1$–C$_6$ alkyl group, R$^5$ is a hydrogen atom, a C$_1$–C$_6$ alkyl group, a C$_1$–C$_6$ haloalkyl group, a C$_2$–C$_6$ alkenyl group or a C$_2$–C$_6$ alkynyl group, and Y$^2$ is —O—, —S— or —NH—),

—COOCH(R$^4$)CO—Y$^1$R$^5$ (wherein R$^4$, R$^5$ and Y$^1$ are as defined above), or

—COOR$^6$ (wherein R$^6$ is a C$_1$–C$_6$ alkyl group, a C$_2$–C$_6$ alkenyl group or a C$_2$–C$_6$ alkynyl group), R$^1$ is a C$_1$–C$_6$ alkyl group, R$^2$ is a hydrogen atom, a C$_1$–C$_6$ alkyl group or a C$_1$–C$_6$ haloalkyl group, X$^1$ and X$^2$, which may be the same or different, are halogen atoms, Y is —O—, —S—, —SO— or —SO$_2$—, and n is zero or 1, said herbicidal composition further comprising as an additive(s) at least one anionic surfactant selected from the following:
polyoxyethylene styryl phenyl ether sulfates, polyoxyethylene styryl phenyl ether phosphates, C$_8$–C$_{18}$ alkyl sulfates, polycarbonates, condensation products of cresol and formaldehyde, and fatty acid alkyltaurines.

2. A method of reducing phytotoxicity according to claim 1, wherein the anionic surfactant(s) is at least one selected from the group consisting of polyoxyethylene styryl phenyl ether sulfates, and polyoxyethylene styryl phenyl ether phosphates.

3. A method of reducing phytotoxicity according to claim 1, wherein the anionic surfactant(s) is contained in an amount of 0.1 to 80 parts by weight per 100 parts by weight of the herbicidal composition.

4. A method of reducing phytotoxicity to barley, which comprises applying to said barley, herbicidal compositions comprising as an active ingredient at least one compound selected from 3-substituted phenylpyrazole derivatives represented by the general formula (I):

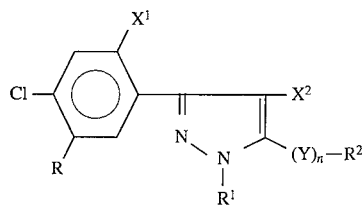

wherein R is

—Y$^1$R$^3$ (wherein R$^3$ is a C$_1$–C$_6$ alkyl group, a C$_1$–C$_6$ haloalkyl group, a C$_2$–C$_6$ alkenyl group or a C$_2$–C$_6$ alkynyl group, and Y$^1$ is —O— or —S—),

—Y$^2$CH(R$^4$)CO—OR$^5$ wherein R$^4$ is a hydrogen atom or a C$_1$–C$_6$ alkyl group, R$^5$ is a hydrogen atom, a C$_1$–C$_6$ alkyl group, a C$_1$–C$_6$ haloalkyl group, a C$_2$–C$_6$ alkenyl group or a C$_2$–C$_6$ alkynyl group, and Y$^2$ is —O—, —S— or —NH—),

—COOCH(R$^4$)CO—Y$^1$R$^5$ (wherein R$^4$, R$^5$ and Y$^1$ are as defined above), or

—COOR$^6$ (wherein R$^6$ is a C$_1$–C$_6$ alkyl group, a C$_2$–C$_6$ alkenyl group or a C$_2$–C$_6$ alkynyl group), R$^1$ is a C$_1$–C$_6$ alkyl group, R$^2$ is a hydrogen atom, a C$_1$–C$_6$ alkyl group or a C$_1$–C$_6$ haloalkyl group, X$^1$ and X$^2$, which may be the same or different, are halogen atoms, Y is —O—, —S—, —SO— or —SO$_2$—, and n is zero or 1, said herbicidal composition further comprising as an additive(s) at least one anionic surfactant selected from the following:
polyoxyethylene styryl phenyl ether sulfates, polyoxyethylene styryl phenyl ether phosphates, C$_8$–C$_{18}$ alkyl sulfates, polycarbonates, condensation products of cresol and formaldehyde, and fatty acid alkyltaurines.

5. A method of reducing phytotoxicity to wheat, which comprises applying to said wheat, herbicidal compositions comprising as an active ingredient at least one compound selected from 3-substituted phenylpyrazole derivatives represented by the general formula (I):

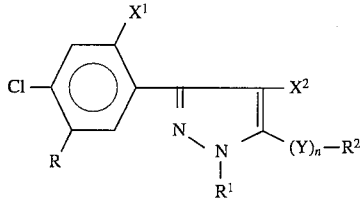

wherein R is

—Y$^1$R$^3$ (wherein R$^3$ is a C$_1$–C$_6$ alkyl group, a C$_1$–C$_6$ haloalkyl group, a C$_2$–C$_6$ alkenyl group or a C$_2$–C$_6$ alkynyl group, and Y$^1$ is —O— or —S—),

—Y$^2$CH(R$^4$)CO—OR$^5$ wherein R$^4$ is a hydrogen atom or a C$_1$–C$_6$ alkyl group, R$^5$ is a hydrogen atom, a C$_1$–C$_6$ alkyl group, a C$_1$–C$_6$ haloalkyl group, a $C_2$–$C_6$ alkenyl group or a $C_2$–$C_6$ alkynyl group, and $Y^2$ is —O—, —S— or —NH—),

—COOCH($R^4$)CO—$Y^1R^5$ (wherein $R^4$, $R^5$ and $Y^1$ are as defined above), or

—COO$R^6$ (wherein $R^6$ is a $C_1$–$C_6$ alkyl group, a $C_2$–$C_6$ alkenyl group or a $C_2$–$C_6$ alkynyl group), $R^1$ is a $C_1$–$C_6$ alkyl group, $R^2$ is a hydrogen atom, a $C_1$–$C_6$ alkyl group or a $C_1$–$C_6$ haloalkyl group, $X^1$ and $X^2$, which may be the same or different, are halogen atoms, Y is —O—, —S—, —SO— or —$SO_2$—, and n is zero or 1, said herbicidal composition further comprising as an additive(s) at least one anionic surfactant selected from the following:

polyoxyethylene styryl phenyl either sulfates, polyoxyethylene styryl phenyl either phosphates, $C_8$–$C_{18}$ alkyl sulfates, polycarbonates, condensation products of cresol and formaldehyde, and fatty acid alkyltaurines.

* * * * *